United States Patent [19]

Teramoto

[11] 4,159,057
[45] Jun. 26, 1979

[54] SEALED SAMPLE CAPSULE USED FOR THERMAL ANALYZER

[75] Inventor: Yoshihiko Teramoto, Shizuoka, Japan

[73] Assignee: Kabushiki Kaisha Daini Seikosha, Japan

[21] Appl. No.: 852,550

[22] Filed: Nov. 17, 1977

Related U.S. Application Data

[63] Continuation-in-part of Ser. No. 777,827, Mar. 15, 1977, abandoned, which is a continuation of Ser. No. 559,576, Mar. 18, 1975, abandoned.

[51] Int. Cl.² .................. B65D 7/34; B65D 17/00; B65D 85/00
[52] U.S. Cl. .................. 206/525; 73/15 B; 220/3
[58] Field of Search ............. 206/525, 527, 3; 220/3; 73/15 B

[56] References Cited

U.S. PATENT DOCUMENTS

| | | | |
|---|---|---|---|
| 2,664,998 | 1/1954 | Gifford et al. | 206/527 |
| 2,918,003 | 12/1959 | Temple | 206/3 |
| 2,995,009 | 8/1961 | Rush | 206/3 |
| 3,084,534 | 4/1963 | Goton | 206/527 |
| 3,211,286 | 10/1965 | Gaydos | 206/524.8 |
| 3,285,053 | 11/1966 | Mazieres | 73/15 B |
| 3,604,586 | 9/1971 | Baldauf | 220/3 |

Primary Examiner—William T. Dixson, Jr.
Attorney, Agent, or Firm—Robert E. Burns; Emmanuel J. Lobato; Bruce L. Adams

[57] ABSTRACT

A sealed sample capsule for thermal analyzers comprises a vessel and a plug. Sample material to be analyzed is packed in the vessel, the plug is next pushed in upon the material and the upper end portion of the vessel is pressed inwardly to hold the plug in place sealing the capsule. The capsule has a remarkably high capacity to bear internal pressure and can be made of steel or iron which is not affected by such active material as mercury or gallium.

15 Claims, 7 Drawing Figures

SEALED SAMPLE CAPSULE USED FOR THERMAL ANALYZER

RELATED APPLICATIONS

This is a Continuation-in-Part application of prior copending application Ser. No. 777,827 filed on Mar. 15, 1977 and now abandoned, and which was a Continuation application of prior copending application Ser. No. 559,576 filed on Mar. 18, 1975 and now abandoned.

BACKGROUND OF THE INVENTION

The present invention relates to a sealed sample capsule for a scanning-type calorimeter or differential thermal analyzer.

A conventional capsule is illustrated in FIG. 1, and comprises a can "a" having a flange "b" formed on the brim thereof which is covered by a cover plate "c". By cutting off margin "b" of the flange "b" and margin "c" of the plate "c" with a press, the two members are united or intermeshed at the cut-off section so that the capsule is sealed containing sample material "d" therein.

This well-known type of capsule has the merits of being easy to seal and easy to handle in use, but it has, on the other hand, demerits in that it will easily break or be distorted and consequently leak the sample material under higher internal pressure. The capsule cannot withstand over 3 atmospheres of internal pressure and will not remain sealed at internal pressures higher than that value.

The capsule illustrated in FIG. 1 should be made of silver, aluminium, copper or the like, as good sealing efficiency is required at the intermeshing portion thereof and therefore the capsule is unusable for active material as mercury, gallium and the like.

BRIEF SUMMARY OF THE INVENTION

An object of the present invention is to provide a sealed sample capsule which is able to bear higher internal pressure and which may be composed of a wider variety of materials than prior art capsules.

The capsule of this invention is a sealed sample capsule for thermal analyzers and comprises a vessel for receiving and holding a sample material and a plug pushed into said vessel upon the sample material, the upper brim of said vessel being pressed inwardly to hold the plug.

DESCRIPTION OF THE INVENTION

Figure 1:
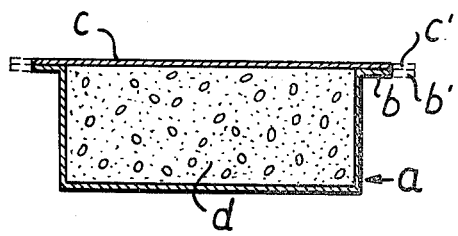
FIG. 1 is a sectional view showing a conventional capsule.
Figure 2:
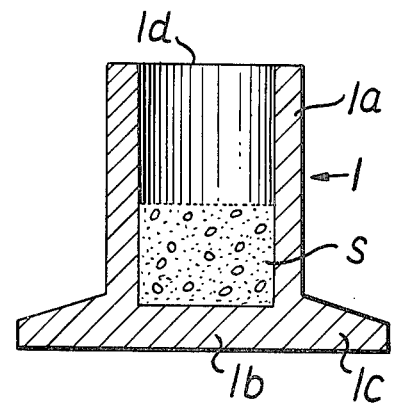
FIGS. 2-4 are sectional views showing a manufacturing process for forming the capsule of the present invention.

Referring more particularly to the drawings, numeral 1 designates a vessel having a cylinder sidewall portion 1a, a bottom portion 1b and a flange 1c which serves the purpose of enabling the vessel to stand upright. A plug 2 is pushed into the cylinder portion 1a and is held in place by the upper brim 1d of the cylinder 1 thereby packing sample material s in the vessel.

Figure 3:
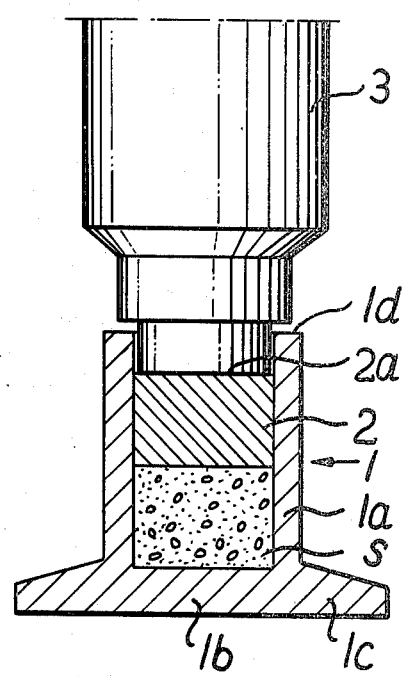
Figure 4:
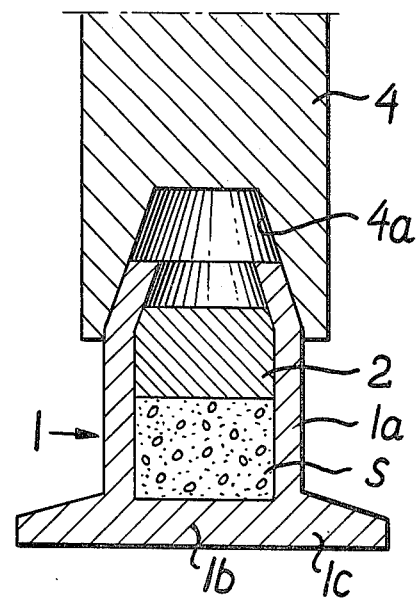

To form the sealed sample capsule, a dose of sample material s is placed in the lower half portion of the capsule chamber formed by the cylinder and bottom portions. Referring to FIG. 3, a pusher 3 pushes the plug 2 into the vessel 1 and the plug 2 has a diameter close to that of the inner diameter of the cylinder portion 1a so that it fits snugly with a tight fit in the vessel 1. The plug 2 is pushed into the vessel 1 such that the plug upper surface 2a is spaced below the upper end surface 1d of the cylinder 1a. Referring to FIG. 4, a pressing or swaging tool 4, which has a tapered bore 4a at the nose thereof, presses downwardly on the vessel 1 and due to the tapered bore, the tool 4 applies radial inward pressure to the upper portion of the cylinder 1a causing the cylinder brim 1d to deform or swage inwardly into a tapered section together with the top portion of the plug 2 so that the capsule becomes sealed containing therein the sample materials.

The plug 2 is required to be thick enough so as not to be bent or wrinkled by the radial force derived from the pushing or pressing action of the tool 4.

Figure 5:
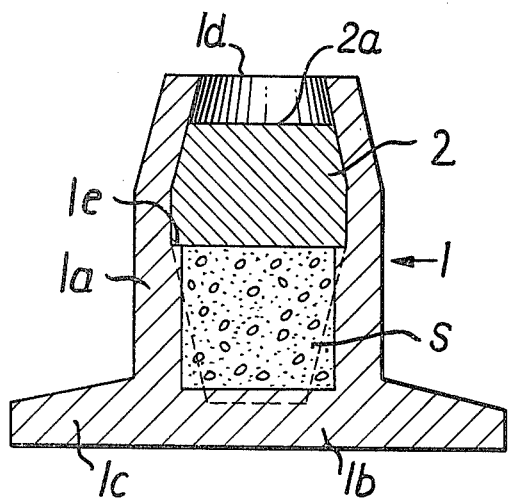
FIG. 5 is a sectional view showing a complete capsule of the present invention.

The vessel 1 preferably has an annular shoulder 1e at the middle of the cylinder inner side wall 1a, as is shown in FIG. 5, or has a tapered inner sidewall, as is illustrated with a dotted line in FIG. 5, which makes it easier to position the plug 2 at the proper position in the vessel by stopping the plug from undergoing further penetration toward the vessel bottom.

As has been described, the capsule of the present invention is perfectly sealed, packing sample material therein, and is formed by inward pressing of the upper end portion of the vessel to deform and hold the plug in place and the capsule has a remarkably high capacity to bear internal pressure.

Figure 6B:
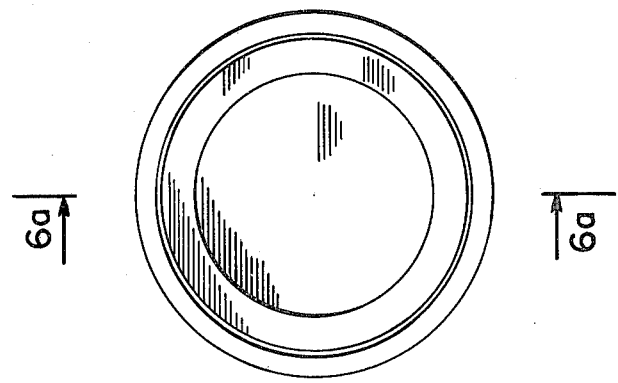
FIGS. 6a and 6b illustrate a vessel with representative dimensions for the capsule according to the present invention.
Figure 6A:
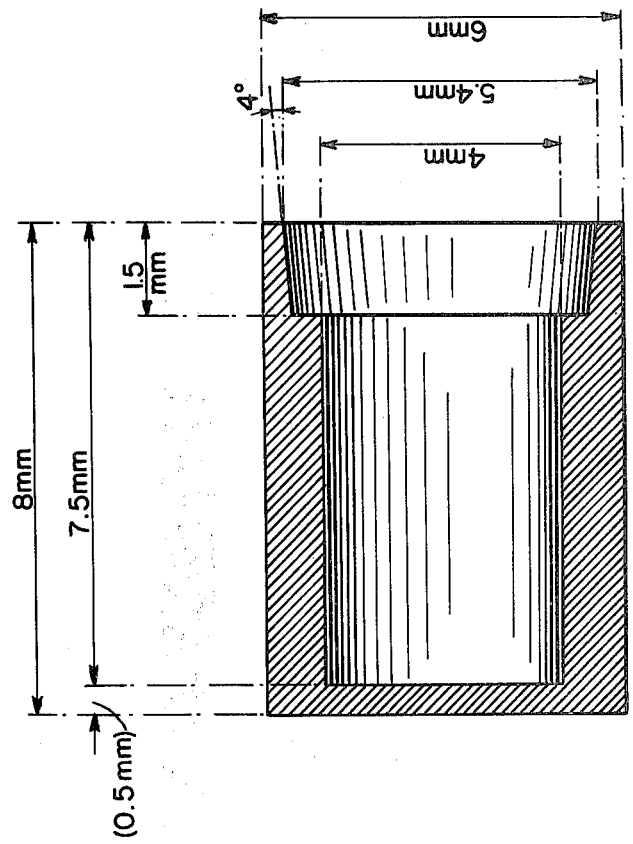

An example of the capsule according to the present invention has been constructed and tested. The tested embodiment had the structure shown in FIG. 6 and was fabricated from aluminum type A2B5056 (under Japanese Industrial Standard H4040 comprising: Cu 0.0–0.10%; Si 0.0–0.30%; Fe 0.0–0.40%; Mn 0.05–0.20%; Mg 4.5–5.6%; Zn 0.0–0.10%; Cr 0.05–0.20%; the rest Al), and silver. The dimensions of the tested embodiment were as follows:

| Capsule Dimensions | |
| --- | --- |
| outer diameter: | 6.0 mm |
| inner diameter (below plug seat): | 4.0 mm |
| inner diameter (above plug seat): | 5.4 mm |
| sidewall thickness (below plug seat): | 1.0 mm |
| sidewall thickness (above plug seat): | 0.3 mm |
| bottom wall thickness: | 0.5 mm |
| distance from interior bottom to plug seat: | 6.0 mm |
| Plug Dimensions | |
| thickness: | 1.2 mm |
| diameter: | 5.5 mm |
| thickness/diameter ratio: | 0.218 |

The capsule was tested in a sealed condition with a sample of distilled water sealed within the capsule assembly. The sealed capsule with the sample of distilled water was heated and the temperature thereof was monitored. A sharp endothermic reaction was observed at approximately 278° C. (532° F.), and at this point seal breakdown of the capsule occurred. The saturated vapor pressure of water vapor at 278° C. is approximately sixty atmospheres so that the tested embodiment of the invention was able to withstand an internal pressure of about sixty atmospheres before seal breakdown. This is about twenty times greater than the internal pressure which the above prior art capsule can withstand. In order to form a seal able to withstand internal pressures on the order of sixty atmospheres, the thickness/diameter ratio of the plug should be on the order of 0.200.

The capsule according to the present invention is not limited to the aluminum capsule material used for the tested embodiment, nor is it limited to aluminum in general. It may be made of steel, iron or the like and is therefore suitable for testing active materials such as mercury or gallium.

What is claimed is:

1. A sealed sample capsule for thermal analyzers comprising: a vessel having an annular sidewall portion terminating at one end in an annular brim portion which defines the vessel top, and a bottom portion connected to the other end of said sidewall portion and defining the vessel bottom; a sample material disposed within said vessel; a plug inserted into and closing the vessel top, said vessel having an annular shoulder disposed about the inner periphery of said sidewall portion at a predetermined distance from the vessel top and being effective to limit the depth of insertion of said plug, and said plug being seated on said annular shoulder; and means defining a seal sealing together said plug and vessel with sufficient tightness to enable said vessel to withstand internal pressures on the order of 60 atmospheres without leakage during thermal analysis of said sample material, said means defining a seal comprising a radially inwardly deformed tapered section of said brim portion tapering in a direction towards the vessel top and being deformed inwardly with sufficient tightness against said plug to form therewith said seal.

2. A sealed sample capsule according to claim 1; wherein said plug has at its top portion a tapered section formed by the radial inward deformation of said brim portion and coacting therewith to form said seal.

3. A sealed sample capsule according to claim 1; wherein said tapered section extends continuously around the circumference of said brim portion.

4. A sealed capsule according to claim 1; wherein said vessel sidewall portion has a tapered inner wall tapering in a direction toward the vessel bottom and being effective to limit the depth of insertion of said plug.

5. A sealed sample capsule according to claim 1; wherein said vessel and plug are composed of a suitable material which does not react with mercury or gallium.

6. A sealed sample capsule according to claim 5; wherein said suitable material comprises steel or iron.

7. A sealed sample capsule according to claim 1, wherein said annular sidewall portion has a thickness on the order of 0.9 to 1.0 mm.

8. A sealed sample capsule according to claim 1, wherein said bottom portion has a thickness on the order of 0.5 mm.

9. A sealed sample capsule according to claim 1, wherein said plug has a thickness/diameter ratio on the order of 0.2.

10. A method of forming a sealed sample capsule comprising the steps of: providing an open-ended vessel and a plug dimensioned to fit snugly within the open end of said vessel; adding a given quantity of sample material into said vessel; inserting said plug into the open end of said vessel to confine said sample material therewithin; pressing said plug downwardly into said vessel until its top surface lies a given distance below the brim of the open end of said vessel; and thereafter deforming the brim of said vessel radially inwardly against said plug to effectively seal together said vessel and plug.

11. A method according to claim 10; wherein said deforming step seals together said vessel and plug with sufficient tightness to enable said vessel to withstand internal pressures on the order of 60 atmospheres.

12. A method according to claim 10; wherein said deforming step comprises applying sufficient inward radial pressure to the brim of said vessel to effect radial inward deformation of both the vessel brim and said plug to thereby seal them together.

13. A method according to claim 10; wherein said deforming step comprises providing a pressing tool having therein a tapered bore tapering in a direction from the tool surface inwardly into the tool, and advancing said pressing tool downwardly over the brim of said vessel so that said tapered bore presses and deforms said vessel brim radially inwardly against said plug to thereby taper said vessel brim.

14. A sealed sample capsule for thermal analyzers and capable of withstanding high internal pressures, said sealed sample capsule comprising: a vessel having an annular sidewall portion terminating at one end in an annular brim portion which defines the vessel top, a bottom portion connected to the other end of said sidewall portion and defining the vessel bottom, and an internal wall defining an internal bore having a lower portion smooth and free of recesses and protrusions and of a first diameter extending from the vessel bottom a given distance toward the vessel top and the bore having an upper portion smooth and free of recesses and protrusions and of a second diameter greater than the first diameter extending from the lower portion of the bore to the vessel top, the lower portion of the bore and the upper portion of the bore meeting within the bore at the given distance from the vessel bottom and defining an internal shoulder thereat; a plug inserted into the upper portion of the bore and seated on said internal shoulder and closing the vessel top, and said plug having smooth side walls free of recesses and protrusions; and means defining a seal sealing together said plug and said vessel with sufficient tightness to enable said vessel to withstand internal pressures on the order of 60 atmospheres without leakage during thermal analysis of a sample material within said vessel, said means defining a seal consisting essentially of a radially inwardly swaged tapered section of said brim portion tapering in a direction towards the vessel top defining an inwardly tapered portion of the upper portion of the bore and a corresponding tapered top portion of said plug formed by the inwardly tapered portion of the upper portion of the bore with said plug pressed against the inwardly tapered portion of the bore and pressed against said shoulder with sufficient tightness to form said seal.

15. A sealed sample capsule according to claim 14, wherein said plug has a thickness/diameter ratio on the order of 0.2.

* * * * *